(12) United States Patent
O'Keefe et al.

(10) Patent No.: US 8,481,255 B2
(45) Date of Patent: Jul. 9, 2013

(54) SCYTOVIRIN DOMAIN 1 RELATED POLYPEPTIDES

(75) Inventors: Barry R. O'Keefe, Frederick, MD (US); Chang-yun Xiong, Bloomingdale, NJ (US); James B. McMahon, Frederick, MD (US); Andrew Byrd, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/250,309

(22) Filed: Sep. 30, 2011

(65) Prior Publication Data
US 2012/0053116 A1    Mar. 1, 2012

Related U.S. Application Data

(62) Division of application No. 11/914,833, filed as application No. PCT/US2006/020100 on May 24, 2006, now Pat. No. 8,067,530.

(60) Provisional application No. 60/684,353, filed on May 25, 2005.

(51) Int. Cl.
| | |
|---|---|
| *C12Q 1/70* | (2006.01) |
| *A61P 31/14* | (2006.01) |
| *A61P 31/12* | (2006.01) |
| *A61P 31/18* | (2006.01) |
| *A61K 38/00* | (2006.01) |
| *A61K 36/02* | (2006.01) |
| *A61K 38/16* | (2006.01) |
| *A01N 37/18* | (2006.01) |
| *C07K 14/405* | (2006.01) |
| *C07K 17/00* | (2006.01) |
| *C07K 17/08* | (2006.01) |
| *C07K 2319/00* | (2006.01) |
| *C07K 2319/31* | (2006.01) |

(52) U.S. Cl.
USPC .............. 435/5; 514/1.1; 514/2.3; 514/3.7; 514/3.8; 530/300; 530/324; 530/402

(58) Field of Classification Search
None
See application file for complete search history.

(56) References Cited

FOREIGN PATENT DOCUMENTS
WO    WO 03/097814 A2    11/2003

OTHER PUBLICATIONS

Shenoy et al. Selective Interactions of the Human Immunodeficiency Virus-Inactivating Protein Cyanovirin-N with High-Mannose Oligosaccharides on gp120 and Other Glycoproteins. The Journal of Pharmacology and Experimental Therapeutics 2001, vol. 297, No. 2, p. 704-710.*

Adams et al., "Oligosaccharide and glycoprotein microarrays as tools in HIV glycobiology: glycan-dependent gp120/protein interactions," *Chem. Biol.*, 11: 875-881 (2004).

Bokesch et al., "A potent novel anti-HIV protein from the cultured cyanobacterium *Scytonema varium*," *Biochemistry*, 42: 2578-2584 (2003).

Gao et al., "Effect of a Single Amino Acid Change in MHC Class I Molecules on the Rate of Progression to AIDS," *The New England Journal of Medicine*, 344 (22): 1668-1675 (2001).

Pakula et al., "Genetic Analysis of Protein Stability and Function," *Annual Review of Genetics*, 23: 289-310 (1989).

International Search Report PCT/US2006/020100 mailed Dec. 20, 2006 (6 pages).

* cited by examiner

*Primary Examiner* — Louise Humphrey

(74) *Attorney, Agent, or Firm* — Leydig, Voit & Mayer, Ltd.

(57) ABSTRACT

A scytovirin domain 1 (SD1) polypeptide, a nucleic acid encoding the polypeptide, and related fusion proteins, conjugates, isolated cells, vectors, and antibodies, as well as a method of inhibiting a viral infection using the same.

15 Claims, 2 Drawing Sheets

Binding to HIV-1 gp120: SD1 vs. Scytovirin*

Scy (1-48) domain can bind to gp120

Figure 2

*Binding determined by ELISA utilizing recombinant gp120, recombinant SD1 and scytovirin and rabbit polyclonal anti-scytovirin antibodies.

```
SEQUENCE LISTING

<160> NUMBER OF SEQ ID NOS: 5

<210> SEQ ID NO 1
<211> LENGTH: 48
<212> TYPE: PRT
<213> ORGANISM: Artificial Sequence
<220> FEATURE:
<223> OTHER INFORMATION: Synthetic

<400> SEQUENCE: 1

Gly Ser Gly Pro Thr Tyr Ser Trp Asn Glu Ala Asn Asn Pro Gly Gly
1               5                   10                  15

Pro Asn Arg Cys Ser Asn Asn Lys Gln Cys Asp Gly Ala Arg Thr Cys
            20                  25                  30

Ser Ser Ser Gly Phe Cys Gln Gly Thr Ser Arg Lys Pro Asp Pro Gly
        35                  40                  45

<210> SEQ ID NO 2
<211> LENGTH: 48
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Xaa can be any amino acid except cysteine

<400> SEQUENCE: 2

Gly Ser Gly Pro Thr Tyr Xaa Trp Asn Glu Ala Asn Asn Pro Gly Gly
1               5                   10                  15

Pro Asn Arg Cys Ser Asn Asn Lys Gln Cys Asp Gly Ala Arg Thr Cys
            20                  25                  30

Ser Ser Ser Gly Phe Cys Gln Gly Thr Ser Arg Lys Pro Asp Pro Gly
        35                  40                  45

<210> SEQ ID NO 3
<211> LENGTH: 144
```

```
<212> TYPE: DNA
<213> ORGANISM: Artificial Sequence
<220> FEATURE:
<223> OTHER INFORMATION: Synthetic

<400> SEQUENCE: 3
ggttctggtc cgacctactc ttggaacgaa gcgaacaacc cgggtggtcc gaaccgttgc      60
tctaacaaca aacagtgcga cggtgcgcgt acctgctctt cttctggttt ctgccagggt     120
acctctcgta aaccggaccc gggg                                            144

<210> SEQ ID NO 4
<211> LENGTH: 95
<212> TYPE: PRT
<213> ORGANISM: Scytonema varium

<400> SEQUENCE: 4

Gly Ser Gly Pro Thr Tyr Cys Trp Asn Glu Ala Asn Asn Pro Gly Gly
1               5                   10                  15

Pro Asn Arg Cys Ser Asn Asn Lys Gln Cys Asp Gly Ala Arg Thr Cys
            20                  25                  30

Ser Ser Ser Gly Phe Cys Gln Gly Thr Ser Arg Lys Pro Asp Pro Gly
        35                  40                  45

Pro Lys Gly Pro Thr Tyr Cys Trp Asp Glu Ala Lys Asn Pro Gly Gly
    50                  55                  60

Pro Asn Arg Cys Ser Asn Ser Lys Gln Cys Asp Gly Ala Arg Thr Cys
65                  70                  75                  80

Ser Ser Ser Gly Phe Cys Gln Gly Thr Ala Gly His Ala Ala Ala
            85                  90                  95

<210> SEQ ID NO 5
<211> LENGTH: 15
<212> TYPE: PRT
<213> ORGANISM: Artificial Sequence
<220> FEATURE:
<223> OTHER INFORMATION: Synthetic

<400> SEQUENCE: 5

Gly Gly Gly Gly Ser Gly Gly Gly Gly Ser Gly Gly Gly Gly Ser
1               5                   10                  15
```

US 8,481,255 B2

SCYTOVIRIN DOMAIN 1 RELATED POLYPEPTIDES

CROSS REFERENCE TO RELATED APPLICATIONS

This application is a divisional application of U.S. patent applicant Ser. No. 11/914,833, filed Dec. 7, 2007, now U.S. Pat. No. 8,067,530, which is the U.S. National Phase of International Patent Application No. PCT/U.S. 06/20100, filed May 24, 2006, now WO 2006/127822, which claims the benefit of U.S. Provisional Patent Application No. 60/684, 353, filed May 25, 2005, all of which are hereby incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 2,998 Byte ASCII (Text) file named "708802SeqListing ST25.txt" created on Oct. 17, 2011.

BACKGROUND OF THE INVENTION

Viral infections remain among the most formidable causes of human and non-human animal morbidity and mortality worldwide. Effective preventions or therapies against most viral pathogens remain elusive. One of the most contemporary and catastrophic examples is the still rapidly expanding and pervasive worldwide pandemic of HIV (human immunodeficiency virus) infection and AIDS (acquired immune deficiency syndrome). Despite more than two decades of research to find effective preventative or therapeutic vaccines or drugs, surprisingly little progress has been made. The need for new effective preventative and therapeutic agents for HIV/AIDS and other potentially lethal viral diseases remains an urgent global priority.

Peptidic molecules offer tremendous structural diversity that can be exploited for development of novel therapeutics and preventions of many different kinds of diseases. For example, in the field of HIV therapeutics a novel, rationally-constructed peptide molecule known as T-20 (Kilby, *Nat. Med.*, 4: 1302-1307 (1998)) has been recently shown to be a potent inhibitor of HIV/cell fusion. Furthermore, naturally occurring, non-mammalian peptides and proteins offer new avenues for antiviral discovery and development. An outstanding example is the remarkable HIV-inactivating protein cyanovirin-N (Boyd et al., *Antimicrob. Agents Chemother.*, 41: 1521-1530 (1997)). Additionally, International Published Application WO 03/097814 (Boyd et al.) and Bokesch et al. (*Biochem.*, 42: 2578-2584 (2003)) disclose the discovery of antiviral scytovirin. Clearly, there is great untapped potential for discovery and development of novel, polypeptides and proteins that can be used in prevention and therapeutics of viral diseases.

The present invention provides new antiviral polypeptides and proteins, fusion proteins, and conjugates, as well as nucleic acids, vectors, host cells, and related compositions and methods of use thereof to inhibit viral infections. These and other aspects and advantages of the present invention, as well as additional inventive features, will become apparent from the description provided herein.

BRIEF SUMMARY OF THE INVENTION

The invention provides a polypeptide comprising an amino acid sequence that has 65% or greater sequence identity to SEQ ID NO: 1, provided that the polypeptide does not comprise SEQ ID NO: 4. The invention also provides a fusion protein and conjugate comprising the polypeptide, as well as a nucleic acid comprising a nucleic acid sequence encoding the polypeptide and an isolated cell comprising the nucleic acid.

The invention further provides an antibody that binds to the polypeptide, wherein the antibody binding site is part of the amino acid sequence that has 65% or greater sequence identity to SEQ ID NO: 1. A composition comprising (i) the polypeptide, fusion protein, conjugate, nucleic acid, isolated cell, or antibody, and (ii) a carrier, excipient, or adjuvant therefore, also is provided herein.

The invention provides methods of using the above compounds and compositions for inhibiting a viral infection. One aspect of the invention provides a method of inhibiting a viral infection in a host, which method comprises administering to the host a viral infection-inhibiting amount of at least one member of the group consisting of the (i) polypeptide, (ii) fusion protein, (iii) conjugate, (iv) nucleic acid, (v) isolated cell, (vi) antibody, or (vii) composition of the invention, which method, optionally, further comprises the prior, simultaneous, or subsequent administration, by the same route or a different route, of a substance other than (i)-(vii) that is efficacious in inhibiting the viral infection, whereupon the viral infection is inhibited.

Another aspect of the invention provides a method of inhibiting the infection of a host by a virus, which method comprises administering to the host the antibody of the invention in an amount sufficient to induce in the host an immune response to the virus, which method, optionally, further comprises the prior, simultaneous, or subsequent administration, by the same or a different route, of a substance other than the antibody that is efficacious in inhibiting the virus or inducing an immune response to the virus, whereupon the infection of the host by the virus is inhibited.

In yet another aspect, the invention provides a method of inhibiting a virus in a biological sample or in/on an inanimate object, which method comprises contacting the biological sample or the inanimate object with a viral-inhibiting amount of at least one of the (i) polypeptide, (ii) fusion protein, or (iii) conjugate of the invention. The method, optionally, further comprises the prior, simultaneous, or subsequent contacting, in the same manner or in a different manner, of the biological sample or inanimate object with a substance other than (i)-(iii) that is efficacious in inhibiting the virus, whereupon the virus is inhibited.

BRIEF DESCRIPTION OF THE DRAWING(S)

FIG. 2 is a graph of absorbance at 450 nm versus concentration (μg/mL) of scytovirin (▲) or SD1 [scy(1-48)] (+), which illustrates scytovirin and SD1 binding to HIV-1 gp120.

DETAILED DESCRIPTION OF THE INVENTION

Polypeptide, Fusion Protein, and Conjugate

Figure 1:
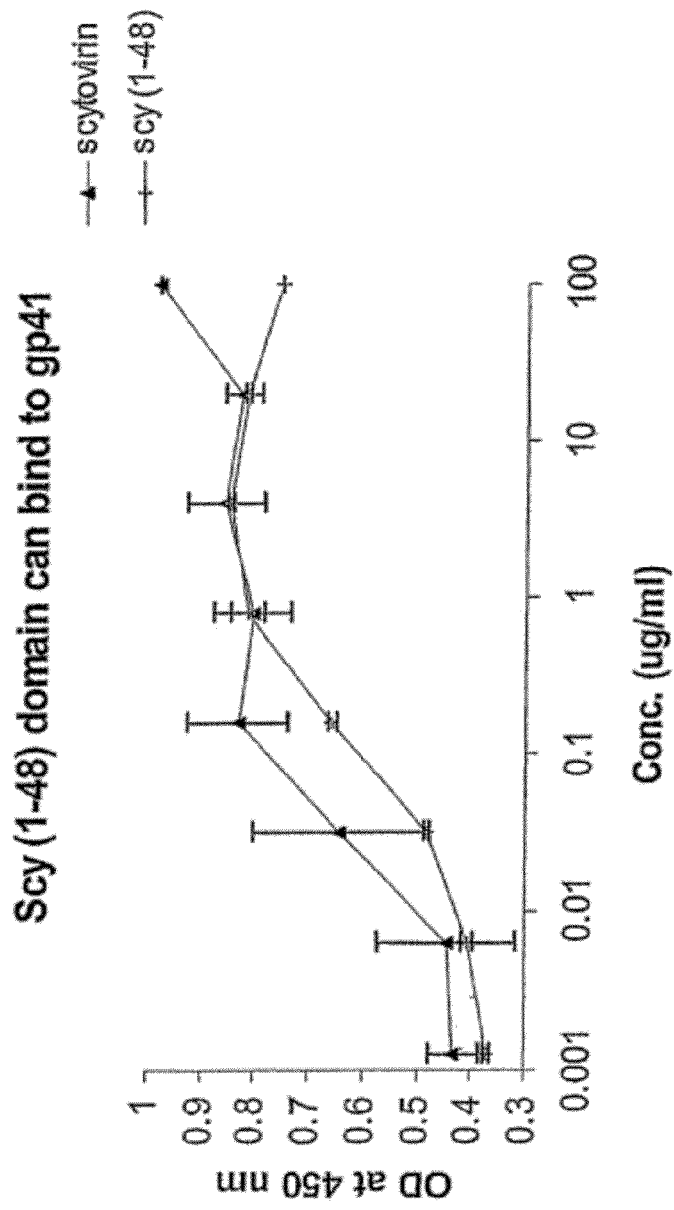
FIG. 1 is a graph of absorbance at 450 nm versus concentration (μg/mL) of scytovirin (▲) or SD1 [scy(1-48)] (+), which illustrates scytovirin and SD1 binding to HIV-1 gp41 ectodomain.

The invention provides a polypeptide comprising an amino acid sequence that has 65% or greater sequence identity to SEQ ID NO: 1, provided that the polypeptide does not comprise SEQ ID NO: 4. SEQ ID NO: 4 sets forth the amino acid sequence of the scytovirin polypeptide and SEQ ID NO: 1 sets forth an amino acid sequence derived from the scytovirin polypeptide that has biological properties similar to the scytovirin polypeptide. In particular, SEQ ID NO: 1 is derived from amino acids 1-48 of scytovirin, which is referred to herein as scytovirin domain 1 (SD1). Accordingly, SEQ ID NO: 1 (e.g., a polypeptide consisting of SEQ ID NO: 1) is therefore referred to as SD1. The polypeptide of the invention is based on a portion of the scytovirin polypeptide (SEQ ID NO: 4) that has antiviral properties. In this regard, the polypeptide of the invention desirably has the ability to bind viral proteins (e.g., gp41 or gp120 of an immunodeficiency virus (e.g., HIV)) and/or exhibit antiviral activity against HIV or other viruses (Ebola, influenza, etc.). More preferably, the polypeptide of the invention has biological affinity for viral proteins such as gp41 or gp120, or antiviral activity) comparable to or greater than that of scytovirin.

"Antiviral" or "antiviral activity" as used herein, both with respect to the polypeptide of the invention and other components or compositions of the invention described herein, refers to the ability of a compound to inhibit a virus. Inhibition of a virus encompasses slowing or stopping the rate of replication or infection of a virus (e.g., within an organism), reducing the infectivity of the virus (e.g., HIV), or inhibiting or preventing the virus from invading a host (e.g., by inducing an immune response in the host). Thus antiviral activity encompasses the activity of a substance or molecule directly against the virus (e.g., by binding viral proteins) or indirectly (e.g., by inducing an immune response). Antiviral activity can be demonstrated by any suitable method, such as by in vitro antiviral assays (e.g., Gulakowski et al., *J. Virol. Methods*, 33: 87-100 (1991), which accurately predict for antiviral activity in humans. Such assays measure the ability of compounds to prevent the replication of HIV and/or the cytopathic effects of HIV on human target cells. These measurements directly correlate with the pathogenesis of HIV-induced disease in vivo.

The terms "sequence identity" and "percent identity" of a sequence (amino acid or nucleic acid sequence), as used herein, means the percent of amino acids that are identical between two optimally aligned sequences. Optimal alignment can be calculated by any of several known algorithms. For the purposes of the invention, the sequence identity is determined using the well-known Basic Local Alignment Search Tool (BLAST), which is publicly available through the National Cancer Institute/National Institutes of Health (Bethesda, Md.) and has been described in printed publications (see, e.g., Altschul et al., *J. Mol. Biol.*, 215(3), 403-10 (1990)).

The polypeptide of the invention can comprise an amino acid sequence that has 65% or greater sequence identity to SEQ ID NO: 1, provided that the polypeptide does not comprise the amino acid sequence of SEQ ID NO: 4. However, it is preferred that the polypeptide comprises an amino acid sequence that has a higher percent identity to SEQ ID NO: 1, for example, an amino acid sequence that has 70% or greater (e.g., 75% or greater), more preferably 80% or greater (e.g., 85% or greater) or even 90% or greater (e.g., 95%, 96%, 97%, 98%, or 99%) sequence identity to SEQ ID NO: 1, provided that the polypeptide does not have the amino acid sequence of SEQ ID NO: 4. It is especially preferred that the polypeptide comprises the amino acid sequence of SEQ ID NO: 2, and even more preferred that the polypeptide comprises the amino acid sequence of SEQ ID NO: 1. The polypeptide can comprise D-amino acids, L-amino acids or a mixture of D- and L-amino acids. The D-form of the amino acids, however, is particularly preferred, since a protein comprised of D-amino acids is expected to have a greater retention of its biological activity in vivo, given that the D-amino acids are not recognized by naturally occurring proteases.

Accordingly, the polypeptide of the invention can be a fragment or variant of the polypeptide of SEQ ID NO: 1 (e.g., a polypeptide comprising an amino acid sequence having the aforementioned percent-identity to SEQ ID NO: 1). Such fragments or variants can comprise deletions or substitutions of the amino acid sequence, provided that such deletions and substitutions do not destroy the usefulness of the polypeptide as described herein. The variants encompassed by the invention can comprise, for example, (i) one or more conservative or neutral amino acid substitutions (e.g., 1-20, preferably 1-10, more preferably 1, 2, 3, 4, or 5) and/or (ii) 1-20, preferably 1-10, more preferably 1, 2, 3, 4 or 5, and even more preferably, 1, 2, or 3, amino acid additions at the N-terminus and/or the C-terminus, with the proviso that the variant has activity characteristic of a polypeptide comprising the amino acid sequence of SEQ ID NO: 1 (e.g., antiviral activity) to a greater or lesser extent but not negated. Preferably, the amino acid at position 7 of SEQ ID NO: 1 is not substituted with cysteine. Similarly, fragments of SEQ ID NO: 1 can be any fragment that retains the function of a polypeptide comprising SEQ ID NO: 1 to a greater or lesser extent, but not negated. Such fragments preferably comprise about 5 or more contiguous amino acids (e.g., about 5-30 contiguous amino acids) or about 10 or more contiguous amino acids (e.g., about 15-25 contiguous amino acids) of SEQ ID NO: 1.

Alterations of the amino acid sequence of SEQ ID NO: 1 to produce fragment or variant polypeptides can be done by a variety of methods known to those skilled in the art. For instance, amino acid substitutions can be conveniently introduced into the proteins at the time of synthesis. Alternatively, site-specific mutations can be introduced by ligating into an expression vector a synthesized oligonucleotide comprising the modified site. Alternatively, oligonucleotide-directed, site-specific mutagenesis procedures can be used, such as disclosed in Walder et al., *Gene*, 42: 133 (1986); Bauer et al., *Gene* 37: 73 (1985); Craik, *Biotechniques*, 12-19 (1995); and U.S. Pat. Nos. 4,518,584 and 4,737,462.

It is within the skill of the ordinary artisan to select synthetic and naturally-occurring amino acids that effect conservative or neutral substitutions for any particular amino acids in a given amino acid sequence (e.g., SEQ ID NO: 1). The ordinarily skilled artisan desirably will consider the context in which any particular amino acid substitution is made, in addition to considering the hydrophobicity or polarity of the side-chain, the general size of the side chain and the pK value of side-chains with acidic or basic character under physiological conditions. For example, lysine, arginine, and histidine are often suitably substituted for each other, and more often arginine and histidine are suitably substituted for each other. As is known in the art, this is because all three amino acids have basic side chains, whereas the pK value for the side-chains of lysine and arginine are much closer to each other (about 10 and 12) than to histidine (about 6). Similarly, glycine, alanine, valine, leucine, and isoleucine are often suitably substituted for each other, with the proviso that glycine is frequently not suitably substituted for the other members of the group. This is because each of these amino acids are relatively hydrophobic when incorporated into a polypeptide, but glycine's lack of an α-carbon allows the phi and psi angles of rotation (around the α-carbon) so much conformational freedom that glycinyl residues can trigger changes in conformation or secondary structure that do not often occur when the other amino acids are substituted for each other. Other groups of amino acids frequently suitably substituted for each other include, but are not limited to, the group consisting of glutamic and aspartic acids; the group consisting of phenylalanine, tyrosine and tryptophan; and the group consisting of serine, threonine, and, optionally, tyrosine. Additionally, the ordinarily skilled artisan can readily group synthetic amino acids with naturally-occurring amino acids.

The polypeptide of the invention can be prepared by any of a number of conventional techniques. The polypeptide can be isolated or purified from a naturally occurring source or from a recombinant source. Suitable techniques for producing the recombinant polypeptides are known (for general background see, e.g., Nicholl, in An Introduction to Genetic Engineering, Cambridge University Press: Cambridge (1994), pp. 1-5 & 127-130; Steinberg et al., in Recombinant DNA Technology Concepts and Biomedical Applications, Prentice Hall: Englewood Cliffs, N.J. (1993), pp. 81-124 & 150-162; Sofer, in Introduction to Genetic Engineering, Butterworth-Heinemann, Stoneham, Mass. (1991), pp. 1-21 & 103-126; Old et al., in Principles of Gene Manipulation, Blackwell Scientific Publishers: London (1992), pp. 1-13 & 108-221; and Emtage, in Delivery Systems for Peptide Drugs, Davis et al., eds., Plenum Press: New York (1986), pp. 23-33). For instance, a nucleic acid encoding a desired protein can be subcloned into an appropriate vector using well-known molecular genetic techniques (see, e.g., Maniatis et al., *Molecular Cloning: A Laboratory Manual*, 2nd ed. (Cold Spring Harbor Laboratory, 1989)). The nucleic acid can be transcribed and the protein subsequently translated in vitro. Commercially available kits also can be employed (e.g., such as manufactured by Clontech, Palo Alto, Calif.; Amersham Life Sciences, Inc., Arlington Heights, Ill.; InVitrogen, San Diego, Calif., and the like).

Such polypeptides also can be synthesized using an automated peptide synthesizer in accordance with methods known in the art. Alternatively, the polypeptide can be synthesized using standard peptide synthesizing techniques well-known to those of skill in the art (e.g., as summarized in Bodanszky, *Principles of Peptide Synthesis*, (Springer-Verlag, Heidelberg: 1984)). In particular, the polypeptide can be synthesized using the procedure of solid-phase synthesis (see, e.g., Merrifield, *J. Am. Chem. Soc.*, 85: 2149-54 (1963); Barany et al., *Int. J. Peptide Protein Res.*, 30: 705-739 (1987); and U.S. Pat. No. 5,424,398). If desired, this can be done using an automated peptide synthesizer. Removal of the t-butyloxycarbonyl (t-BOC) or 9-fluorenylmethyloxycarbonyl (Fmoc) amino acid blocking groups and separation of the polypeptide from the resin can be accomplished by, for example, acid treatment at reduced temperature. The polypeptide-containing mixture then can be extracted, for instance, with diethyl ether, to remove non-peptidic organic compounds, and the synthesized polypeptide can be extracted from the resin powder (e.g., with about 25% w/v acetic acid). Following the synthesis of the polypeptide, further purification (e.g., using HPLC) optionally can be done in order to eliminate any incomplete proteins, polypeptides, peptides or free amino acids. Amino acid and/or HPLC analysis can be performed on the synthesized polypeptide to validate its identity.

The overall size of the polypeptide of the invention is not particularly limited. The polypeptide can consist of or consist essentially of, any one or more of the sequences or fragments described herein, in which case the overall size of the polypeptide will correspond, substantially or exactly to the one or more particular sequences or fragments of the invention that are used. Alternatively, the polypeptide will comprise any one or more of the sequences or fragments described herein along with appropriate flanking sequences. Appropriate flanking sequences are those that do not interfere with the function of the polypeptide, and can be selected in accordance with general principals of peptide design known in the art. In this respect, the polypeptide typically will comprise about 1000 or fewer amino acids, such as about 500 or fewer, about 400 or fewer, about 300 or fewer, about 200 or fewer, about 150 or fewer, about 100 or fewer, or even about 50 or fewer amino acids.

Two or more polypeptides of the invention can be linked by a flexible linker. The flexible linker can be any suitable peptide or other molecule or composition that can be used to join two or more polypeptide domains. Peptide linkers preferably comprises about 5 or more amino acids (e.g., about 6 or more, 7 or more, or 9 or more amino acids), more preferably about 10 or more amino acids (e.g., about 11 or more, 12 or more, or 14 or more amino acids), and most preferably about 15 or more amino acids (e.g., about 17 or more, 20 or more, or 25 or more amino acids). Linker sequences, as well as methods for joining polypeptide domains using flexible linkers, are known in the art (see, e.g., Imanishi et al., *Biochem. Biophys. Res. Commun.*, 333(1): 167-173 (2005); Lin et al., *Eur. Cytokine Netw.*, 15(3): 240-246 (2004)). An exemplary linker sequence is GGGGSGGGGSGGGGS (SEQ ID NO: 5).

The polypeptide of the invention can be joined to other biomolecules, such as, for example, proteins, polypeptides, lipids, carbohydrates, prenyl, and acyl moieties, and nucleic acids. For example, it may be preferable to produce the protein as part of a larger fusion protein, either by chemical conjugation, or through genetic means, such as are known to those skilled in the art. In this regard, the invention also provides a fusion protein comprising the polypeptide of the invention and one or more other protein(s) having any desired properties or effector functions, such as cytotoxic or immunological properties, or other desired properties, such as to facilitate isolation, purification, or analysis of the fusion protein. For example, effector components for use in the fusion polypeptide include immunological reagents and toxins. Immunological reagent refers to an antibody, an immunoglobulin, or an immunological recognition element. An immunological recognition element is an element, such as a peptide (e.g., a FLAG octapeptide leader sequence) that can be appended to make a recombinant SD1-FLAG fusion protein, wherein the FLAG element facilitates, through immunological recognition, isolation and/or purification and/or analysis of the polypeptide (or fragment thereof) or variant thereof to which it is attached. A toxin can be any suitable toxin, such as *Pseudomonas* exotoxin. The addition of a toxin or immunological reagent to the polypeptide of the invention can facilitate purification and analysis of the polypeptide (e.g., such as a FLAG-SD1 fusion protein) or for specific targeting to a virus or viral-infected cells (e.g., HIV and/or HIV-infected cells). In these instances, the polypeptide of the invention serves not only as antiviral or as a neutralizing agent but also as a targeting agent to direct the effector activities of the other proteins selectively against a given virus, such as HIV. Thus, for example, a therapeutic agent can be obtained by combining the HIV-targeting function of the polypeptide of the invention with a toxin aimed at neutralizing an infectious virus and/or by destroying cells producing an infectious virus, such as HIV. Similarly, a therapeutic agent can be obtained, which combines the viral-targeting function of a polypeptide of the invention with the multivalency and effector functions of various immunoglobulin subclasses. A preferred fusion protein comprises the polypeptide of the invention and albumin.

The generation of fusion proteins is within the ordinary skill in the art (see, e.g., Chaudhary et al. (1988), supra) and can involve the use of restriction enzyme or recombinational cloning techniques (see, e.g., Gateway™ (Invitrogen, Carlsbad, Calif.)). See, also, U.S. Pat. No. 5,314,995. In a transcriptional gene fusion, the DNA or cDNA will contain its own control sequence directing appropriate production of protein (e.g., ribosome binding site, translation initiation codon, etc.), and the transcriptional control sequences (e.g., promoter elements and/or enhancers) will be provided by the vector. In a translational gene fusion, transcriptional control sequences as well as at least some of the translational control sequences (i.e., the translational initiation codon) will be provided by the vector. In the case of a translational gene fusion, a chimeric protein will be produced.

If desired, the polypeptide or fusion protein of the invention can be modified, for instance, by glycosylation, amidation, carboxylation, or phosphorylation, or by the creation of acid addition salts, amides, esters, in particular C-terminal esters, and N-acyl derivatives of the proteins of the invention. The polypeptide or fusion protein also can be modified to create protein derivatives by forming covalent or noncovalent complexes with other moieties in accordance with methods known in the art. Covalently-bound complexes can be prepared by linking the chemical moieties to functional groups on the side chains of amino acids comprising the proteins, or at the N- or C-terminus. Desirably, such modifications and conjugations do not adversely affect the activity of the polypeptide or fusion protein. While such modifications and conjugations can increase or reduce activity, the activity desirably is not negated and is characteristic of the unaltered polypeptide.

The invention provides a conjugate comprising a polypeptide of the invention and one or more effector components. Conjugates (e.g., viral-targeted conjugates) can be prepared by chemical coupling of the polypeptide of the invention targeting component with the effector component. The most feasible or appropriate technique to be used to construct a given conjugate will be selected based upon consideration of the characteristics of the particular effector molecule selected. For example, with a selected non-proteinaceous effector component, chemical coupling may be the only feasible option for creating the desired conjugate.

Examples of effector components or other functional reagents suitable for chemical coupling to the polypeptide of the invention and thereby used as effector components in the inventive conjugates can include, for example, polyethylene glycol, dextran, an antiviral agent (other than a polypeptide), a solid support matrix, and the like, whose intended effector functions can include one or more of the following: to improve stability of the conjugate; to increase the half-life of the conjugate; to increase resistance of the conjugate to proteolysis; to decrease the immunogenicity of the conjugate; to attach or immobilize a polypeptide of the invention onto a solid support matrix (i.e., in such instance the solid support matrix can be the effector component of the conjugate) (e.g., see, for example, Harris, in Poly(Ethylene Glycol) Chemistry: Biotechnical and Biomedical Applications, Harris, ed., Plenum Press: New York (1992), pp. 1-14). The antiviral agent can be any suitable antiviral agent, including AZT, ddA, ddI, ddC, 3TC gancyclovir, fluorinated dideoxynucleosides, acyclovir, α-interferon, nonnucleoside analog compounds, such as nevirapine (Shih et al., *PNAS*, 88: 9878-9882, (1991)), TIBO derivatives, such as R82913 (White et al., *Antiviral Res.*, 16: 257-266 (1991)), Ro31-8959, BI-RJ-70 (Merigan, *Am. J. Med.*, 90 (Suppl.4A): 8S-17S (1991)), michellamines (Boyd et al., *J. Med. Chem.*, 37: 1740-1745 (1994)) and calanolides (Kashman et al., *J. Med. Chem.*, 35: 2735-2743 (1992)), nonoxynol-9, gossypol and derivatives, gramicidin, cyanovirin-N and functional homologs thereof (Boyd et al. (1997), supra). Other exemplary antiviral compounds include protease inhibitors (see R. C. Ogden and C. W. Flexner, eds., Protease Inhibitors in AIDS Therapy, Marcel Dekker, N.Y., 2001), such as saquinavir (see I. B. Duncan and S. Redshaw, in R. C. Ogden and C. W. Flexner, supra, pp. 27-48), ritonavir (see D. J. Kempf, in R. C. Ogden and C. W. Flexner, supra, pp. 49-64), indinavir (see B. D. Dorsey and J. P. Vacca, in R. C. Ogden and C. W. Flexner, supra, pp. 65-84), nelfinavir (see S. H. Reich, in R. C. Ogden and C. W. Flexner, supra, pp. 85-100), amprenavir (see R. D. Tung, in R. C. Ogden and C. W. Flexner, supra, pp. 101-118), and anti-TAT agents. The solid support matrix can be magnetic beads, a flow-through matrix, or the material of a contraceptive device, such as a condom, diaphragm, cervical cap, vaginal ring, or sponge. In an alternative embodiment, the solid support matrix can be an implant suitable for surgical implantation in a host.

Conjugates can comprise more than one effector component that are the same or different and can have the same or different effector functions. Diverse applications and uses of functional proteins and peptides, such as the polypeptide of the invention attached to or immobilized on a solid support matrix and/or comprising polyethylene glycol conjugated proteins or peptides in a review by Holmberg et al. (In Poly (Ethylene Glycol) Chemistry: Biotechnical and Biomedical Applications, Harris, ed., Plenum Press: New York (1992), pp. 303-324).

Antibodies

The invention also provides an antibody that recognizes (i.e., binds) a polypeptide of the invention. Preferably, the antibody binds to a portion or part of the amino acid sequence having the above-described percent sequence identity (e.g., 65% or greater, 70% or greater, 80% or greater, 85% or greater, 90% or greater, 95% or greater, 96% or greater, 97% or greater, 98% or greater, or 99% or greater) to SEQ ID NO: 1 (e.g., binds to part of SEQ ID NO: 1 or SEQ ID NO: 2). In other words, it is preferable that the antibody binding site is part of the amino acid sequence so defined. The availability of antibodies to any given protein is highly advantageous, as it provides the basis for a wide variety of qualitative and quantitative analytical methods, separation and purification methods, and other useful applications directed to the subject proteins. Antibodies to the polypeptide of the invention can be prepared using well-established methodologies (e.g., such as the methodologies described in detail by Harlow and Lane, in Antibodies. A Laboratory Manual, Cold Spring Harbor Laboratory, Cold Spring Harbor, 1988, pp. 1-725). Such antibodies can comprise both polyclonal and monoclonal antibodies. Furthermore, such antibodies can be obtained and employed either in solution-phase or by coupling the antibodies to a desired solid-phase matrix, such as magnetic beads or a flow through matrix. Such antibodies can be used in conjunction with well-established procedures (e.g., such as described by Harlow and Lane (1988, supra)) for the detection, quantification, or purification of a polypeptide of the invention or fusion protein or conjugate thereof or host cell transformed to produce the same. Such antibodies also can be used in the treatment of a host as described further herein with respect to the methods of the invention.

Preferably, the antibody is anti-idiotypic in respect to gp120, i.e., has an internal image of gp120 of a primate immunodeficiency virus. Preferably, the antibody can compete with gp120 of a primate immunodeficiency virus for binding to a polypeptide of the invention (e.g., a polypeptide comprising SEQ ID NO: 1). In this regard, the primary immunodeficiency virus preferably is HIV (e.g., HIV-1 or HIV-2). Anti-idiotypic antibodies can be generated in accordance with methods known in the art (see, for example, Benjamin, In Immunology: a short course, Wiley-Liss, N.Y., 1996, pp. 436-437; Kuby, In Immunology, 3rd ed., Freeman, N.Y., 1997, pp. 455-456; Greenspan, et al., *FASEB J.,* 7: 437-443 (1993); and Poskitt, *Vaccine,* 9: 792-796 (1991)). For instance, a polypeptide of the invention (e.g., that can bind to gp120) can be directly administered to an animal, such that the animal generates and antibody that has an internal image of gp120. The production of anti-idiotypic antibodies in an animal to be treated is known as anti-idiotype induction therapy, and is described, for example, by Madiyalakan et al. (*Hybridoma,* 14: 199-203 (1995)). Similarly, the antibody can be anti-idiotypic in respect to gp41.

Although nonhuman anti-idiotypic antibodies to gp120 are proving useful as vaccine antigens in humans, in certain instances, the favorable properties of an antibody of the invention might be further enhanced and/or any adverse properties further diminished, through humanization strategies, such as those reviewed by Vaughan (*Nature Biotech.,* 16: 535-539 (1998)).

Nucleic Acid

The invention provides a nucleic acid (e.g., an isolated or purified nucleic acid) comprising a nucleotide sequence encoding a polypeptide of the invention as described herein. Thus, the invention provides a nucleic acid comprising a nucleic acid sequence that encodes an amino acid sequence that has about 65% or greater, 70% or greater, 75% or greater, 80% or greater, 85% or greater, or 90% or greater sequence identity to SEQ ID NO: 1, or encodes the amino acid sequence SEQ ID NO: 1 or SEQ ID NO: 2, or an antiviral fragment of SEQ ID NO: 1, provided that the nucleic acid does not encode the amino acid sequence of SEQ ID NO: 4. The invention also encompasses a nucleic acid encoding a polypeptide or fusion protein comprising such an amino acid sequence, provided it does not encode the amino acid sequence of SEQ ID NO: 4. The term "nucleic acid" as used herein refers to a polymer of DNA or RNA (i.e., a polynucleotide), which can be single-stranded or double-stranded, synthesized or obtained from natural sources, and which can contain natural, non-natural, or altered nucleotides. Desirably, the nucleic acid of the invention encodes a polypeptide comprising the amino acid sequence of SEQ ID NO: 2, and preferably encodes the amino acid sequence SEQ ID NO: 1. A preferred nucleic acid comprises the nucleic acid sequence of SEQ ID NO: 3.

The invention also encompasses a nucleic acid comprising a nucleic acid sequence that is substantially identical to SEQ ID NO: 3. A sequence is substantially identical to SEQ ID NO: 3 if it has about 65% or greater (e.g., about 65% or greater), preferably about 70% or greater (e.g., about 75% or greater), such as about 80% or greater (e.g., about 85% or greater) or even about 90% or greater (e.g., about 95% or greater) sequence identity to SEQ ID NO: 3.

Another indication that polynucleotide sequences are substantially identical is if the first sequence and the complement of the second sequence selectively hybridize to each other under stringent conditions. Stringent conditions are sequence-dependent and will be different in different circumstances. Generally, stringent conditions are selected to be about 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Stringent conditions are defined, for the purposes of the invention, as those conditions that allow up to about 25% mismatch, more preferably up to about 15% mismatch, and most preferably up to about 10% mismatch (e.g., up to 5% mismatch). Hybridization and wash conditions that result in such levels of stringency can be selected by the ordinarily skilled artisan using techniques known in the art.

One of ordinary skill in the art will appreciate, however, that two nucleic acid sequences can have substantially different sequences, yet encode substantially similar, if not identical, amino acid sequences, due to the degeneracy of the genetic code. The invention is intended to encompass such nucleic acids.

A variety of techniques used to synthesize the nucleic acids of the present invention are known in the art. See, for example, Lemaitre et al., *PNAS USA,* 84: 648-652 (1987).

The nucleic acid of the invention can be in the form of a vector. In this regard, the invention provides a vector comprising an above-described nucleic acid. The vector can be targeted to a cell-surface receptor if so desired. A nucleic acid as described above can be cloned into any suitable vector and can be used to transform or transfect any suitable host. The selection of vectors and methods to construct them are commonly known to persons of ordinary skill in the art and are described in general technical references (see, in general, "Recombinant DNA Part D," *Methods in Enzymology,* Vol. 153, Wu and Grossman, eds., Academic Press (1987)). Desirably, the vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

Constructs of vectors, which are circular or linear, can be prepared to contain an entire nucleic acid as described above or a portion thereof ligated to a replication system functional in a prokaryotic or eukaryotic host cell. Replication systems can be derived from ColE1, 2 mu plasmid, λ, SV40, bovine papilloma virus, and the like.

In addition to the replication system and the inserted nucleic acid, the construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

One of ordinary skill in the art will appreciate that any of a number of vectors known in the art are suitable for use in the invention. Suitable vectors include those designed for propagation and expansion or for expression or both. Examples of suitable vectors include, for instance, plasmids, plasmid-liposome complexes, and viral vectors, e.g., parvoviral-based vectors (i.e., adeno-associated virus (AAV)-based vectors), retroviral vectors, herpes simplex virus (HSV)-based vectors, and adenovirus-based vectors. Any of these expression constructs can be prepared using standard recombinant DNA techniques described in, e.g., Sambrook et al., Molecular Cloning: A Laboratory Manual, 2$^{nd}$ edition, Cold Spring Harbor Laboratory Press, Cold Spring Harbor, N.Y. (1989); Ausubel et al., Current Protocols in Molecular Biology, Greene Publishing Associates and John Wiley & Sons, New York, N.Y. (1994); Fischer et al., *Transgenic Res.,* 9(4-5): 279-299 (2000); Fischer et al., *J. Biol. Regul. Homeost. Agents,* 14: 83-92 (2000); deWilde et al., Plant Molec. Biol., 43: 347-359 (2000); Houdebine, *Transgenic Research,* 9: 305-320 (2000); Brink et al., *Theriogenology,* 53: 139-148 (2000); Pollock et al., *J. Immunol. Methods,* 231: 147-157 (1999); Conrad et al., *Plant Molec. Biol.,* 38: 101-109 (1998); Staub et al., *Nature Biotech.,* 18: 333-338 (2000);

McCoimick et al., *PNAS USA* 96: 703-708 (1999); Zeitlin et al., *Nature Biotech.*, 16: 1361-1364 (1998); Tacker et al., *Microbes and Infection*, 1: 777-783 (1999); and Tackett et al., *Nature Med.*, 4(5): 607-609 (1998). Examples of cloning vectors include the pUC series, the pBluescript series (Stratagene, LaJolla, Calif.), the pET series (Novagen, Madison, Wis.), the pGEX series (Pharmacia Biotech, Uppsala, Sweden), and the pEX series (Clonetech, Palo Alto, Calif.). Bacteriophage vectors, such as λGT10, λGT11, λZapII (Stratagene), λ EMBL4, and λ NM1149, also can be used. Examples of plant expression vectors include pBI101, pBI101.2, pBI101.3, pBI121, and pBIN19 (Clonetech, Palo Alto, Calif.). Examples of animal expression vectors include pEUK-C1, pMAM, and pMAMneo (Clonetech).

An expression vector can comprise a native or normative promoter operably linked to a nucleic acid as described above. The selection of promoters, e.g., strong, weak, inducible, tissue-specific and developmental-specific, is within the skill in the art. Similarly, the combining of a nucleic acid as described above with a promoter also is within the skill in the art.

Isolated Cell

The nucleic acid of the invention can be introduced into a cell using suitable techniques (e.g., transfection, electroporation, transduction, micro-injection, transformation, and the like). Thus, the invention provides an isolated cell comprising the above-described nucleic acid of the invention. The nucleic acid can be in the form of a vector, which is optionally targeted to a cell-surface receptor. Suitable host cells include, but are not limited to an animal cells, such as a bird or mammalian cell, particularly a human cell, or a bacterial cell, such as *E. coli* (in particular *E. coli* TB-1, TG-2, DH5α, XL-Blue MRF' (Stratagene), SA2821, and Y1090), *B. subtilis, P. aerugenosa, S. cerevisiae*, and *N. crassa*. Preferably, the cell is a bacterium or yeast. A preferred bacterium is *lactobacillus*.

Compositions

The invention provides a composition (e.g., pharmaceutical composition) comprising (i) a polypeptide, fusion protein, conjugate, nucleic acid, or antibody of the invention (collectively referred to as the compounds of the invention), as described herein, and (ii) a carrier, excipient, or adjuvant therefor. The amount of component (i) present in the composition will depend upon its end use. If the composition is to be used to inhibit a virus, then the composition should comprise an antiviral-effective amount of component (i). If the composition is to be used to induce an immune response in a host, then the composition should comprise an amount of component (i) effective to induce the immune response.

The carrier can be any of those conventionally used and is limited only by chemico-physical considerations, such as solubility and lack of reactivity with the active agent (e.g., the compound of the invention), and by the route of administration. It is preferred that the carrier is pharmaceutically acceptable, and that the pharmaceutically acceptable carrier is chemically inert to the active agent. Preferably, the carrier has few or no detrimental side effects or toxicity under the conditions of use. The pharmaceutically acceptable carriers described herein, for example, vehicles, adjuvants, excipients, and diluents, are well-known to those ordinarily skilled in the art and are readily available to the public. Typically, the composition, such as a pharmaceutical composition, can comprise a physiological saline solution; dextrose or other saccharide solution; or ethylene, propylene, polyethylene, or other glycol.

The composition can further comprise at least one additional active agent. The particular type of additional active agent will, of course, depend upon the end use of the composition. For instance, for the inhibition of a virus, the composition can comprise a substance (other than the compound of the invention) that is efficacious in inhibiting the viral invection. If the composition is to be used to induce an immune response, the composition can further comprise an immuno-adjuvant, such as polyphosphazene polyelectrolyte.

The composition can comprise more than one compound of the invention, or other pharmaceuticals, such as virucides, immunomodulators, immunostimulants, antibiotics, and absorption enhancers. Exemplary immunomodulators and immunostimulants include various interleukins, sCD4, cytokines, antibody preparations, blood transfusions, and cell transfusions. Exemplary antibiotics include antifungal agents, antibacterial agents, and anti-Pneumocystis carnii agents. Exemplary absorption enhancers include bile salts and other surfactants, saponins, cyclodextrins, and phospholipids (Davis (1992), supra).

Method of Inhibiting Viral Infection

The compounds and compositions of the invention as described herein can be used for any purpose. The polypeptide, fusion protein, and conjugate of the invention desirably can bind viral protein, such as gp41 and gp120, rendering these and other compounds and compositions of the invention (e.g., the nucleic acid, antibody, and isolated cell) useful for investigating mechanisms of viral replication, infection, and inhibition. Also, the compounds and compositions of the invention are particularly useful for antiviral purposes. The compounds and compositions of the invention, for example, can be used to inhibit a viral infection in a host and can be used therapeutically or prophylactically. By therapeutically is meant that the host already has been infected with the virus. By prophylactically is meant that the host has not yet been infected with the virus but is at risk of being infected with the virus. Prophylactic treatment is intended to encompass any degree of inhibition of viral infection, including, but not limited to, complete inhibition, as one of ordinary skill in the art will readily appreciate that any degree in inhibition of viral infection is advantageous.

In this regard, the invention provides a method of inhibiting a viral infection in a host, which method comprises administering to the host (e.g., a host comprising a viral infection) a viral infection-inhibiting amount of the polypeptide, fusion protein, conjugate, antibody, nucleic acid, isolated cell, or composition of the invention.

The invention also provides a method of inhibiting the infection of a host by a Virus comprising administering to the host (e.g., a host that has not been infected by the virus) an antibody of the invention in an amount sufficient to induce in the animal an immune response, whereupon the infection of the animal with the virus is inhibited. Alternatively, or in addition to the administration of an antibody of the invention, the method can comprise the administration to the host of a polypeptide, fusion protein, or conjugate of the invention such that antibodies are produced by the host. In yet another aspect, the method can comprise, in addition to or instead of the administration of the antibody and/or polypeptide, fusion protein, or conjugate, the administration of a nucleic acid (or vector or isolated cell comprising the nucleic acid) to the host, such that a polypeptide of the invention is produced by the host, and, consequently antibodies to the polypeptide are produced in the host.

The compounds and compositions of the invention (i.e., the polypeptide, fusion protein, conjugate, nucleic acid, isolated cell, antibody, and compositions comprising same) useful in the inventive methods are as previously described herein.

The virus to be inhibited can be any suitable virus. Preferably, the virus is a retrovirus, such as a primate immunodeficiency virus (e.g., SIV) or HIV (e.g., HIV-1 or HIV-2). However, the invention can be used to inhibit other viruses, as well (see, e.g., Principles of Virology: Molecular Biology, Pathogenesis, and Control, Flint et al., eds., ASM Press: Washington, D.C., 2000, particularly Chapter 19). Examples of viruses include, but are not limited to one or more of the following: Type C and Type D retroviruses, HTLV-1, HTLV-2, FIV, FLV, MLV, BLV, BIV, equine infectious virus, anemia virus, bird viruses, such as bird influenza, SARS, and coronavirus, avian sarcoma viruses, such as Rous sarcoma virus (RSV), hepatitis type A, B, non-A and non-B viruses, arboviruses, varicella viruses, human herpes virus (e.g., HHV-6), measles, mumps and rubella viruses, pox viruses, influenza viruses, such as influenza viruses A and B, Ebola and other hemorrhagic fever viruses, and other viruses. Preferably, the virus to be inhibited comprises as a surface protein (e.g., a coat protein) a glycoprotein having a high mannose oligosaccharide, such as an immunodeficiency virus, in which case the host is preferably human, and the virus is HIV.

The above methods can further comprise the concurrent or pre- or post-treatment with an adjuvant to enhance the antiviral effectiveness of the compounds and compositions of the invention, or to enhance the immune response of the host. For example, the methods can further comprise the prior, simultaneous, or subsequent administration, by the same or a different route, of a substance other than a compound or composition of the invention that is efficacious in inhibiting the virus (e.g., an antiviral agent) or inducing an immune response to the virus (e.g., an immunostimulant). See, for example, Harlow et al., 1988, supra.

With regard to the forgoing methods of the invention, the host can be any suitable animal, such as a bird (e.g., chicken, duck, goose, dove, and the like) or a mammal, such as a cow, horse, primate, pig, goat, cat, dog, rabbit, guinea pig, mouse, rat, hamster, guinea pig, or, most preferably, a human.

The dose administered to a host, such as an animal, in particular a human, in the context of the present invention should be sufficient to effect a prophylactic or therapeutic response in the individual over a reasonable time frame. The dose used to achieve a desired antiviral concentration in vivo (e.g., 0.1 nM, 0.2 nM, 0.5 nM, 1 nM, 10 nM, 50 nM, 100 nM, 200 nM, 400 nM, 500 nM, 600 nM, 800 nM, 1000 nM, or ranges thereof) will be determined by the potency of the particular active agent employed, the severity of the disease state of the infected individual, as well as, in the case of systemic administration, the body weight and age of the infected individual. The size of the dose also will be determined by the existence of any adverse side effects that can accompany the particular active agent employed. It is always desirable, whenever possible, to keep adverse side effects to a minimum. The dosages of ddC and AZT used in AIDS or ARC patients are known in the art. A virustatic range of ddC is generally between 0.05 µM to 1.0 µM. A range of about 0.005-0.25 mg/kg body weight is virustatic in most patients. The preliminary dose ranges for oral administration are somewhat broader, for example, 0.001 to 0.25 mg/kg given in one or more doses at intervals of 2, 4, 6, 8, 12, etc. hours. Currently, 0.01 mg/kg body weight ddC given every 8 hrs is preferred. When given in combined therapy, the other antiviral agent, for example, can be given at the same time as the present inventive active agent or the dosing can be staggered as desired. The two drugs also can be combined in a composition. Doses of each can be less when used in combination than when either is used alone.

In terms of administration of the inventive antiviral agents or conjugates thereof, the dosage can be in unit dosage form, such as a tablet or capsule. The term "unit dosage form" as used herein refers to physically discrete units suitable as unitary dosages for human and animal subjects, each unit containing a predetermined quantity of a compound or composition of the invention, alone or in combination with other active agents, calculated in an amount sufficient to produce the desired effect in association with a pharmaceutically acceptable diluent, carrier, or vehicle.

The specifications for the unit dosage forms of the present invention depend on the particular compound of the invention employed and the effect to be achieved, as well as the associated pharmacodynamics in the host. The dose administered should be an antiviral effective amount or an amount necessary to achieve an effective level in the individual patient.

Since the effective level is used as the preferred endpoint for dosing, the actual dose and schedule can vary, depending upon interindividual differences in pharmacokinetics, drug distribution, and metabolism. The effective level can be defined, for example, as the blood or tissue level (e.g., 0.1-1,000 nM) desired in the patient that corresponds to a concentration of one or more active agents that inhibits a virus, such as HIV, in an assay known to predict for clinical antiviral activity of chemical compounds and biological agents. The effective level for agents of the invention also can vary when the inventive active agent is used in combination with other known active agents or combinations thereof.

One skilled in the art can easily determine the appropriate dose, schedule, and method of administration for the exact formulation of the composition being used, in order to achieve the desired effective concentration in the individual patient. One skilled in the art also can readily determine and use an appropriate indicator of the effective concentration of the compounds of the present invention by a direct (e.g., analytical chemical analysis) or indirect (e.g., with surrogate indicators such as p24 or RT) analysis of appropriate patient samples (e.g., blood and/or tissues).

In the treatment of some virally infected individuals, it can be desirable to utilize a mega-dosing regimen, wherein a large dose of compound or composition of the invention (i.e., active ingredient) is administered, time is allowed for the active ingredient to take effect, and then a suitable reagent, device or procedure is administered to the individual to inactivate or remove the active ingredient.

When the method comprises the administration of an isolated cell of the invention to the host, the isolated cell is desirably a cell from an organism that shares homology with the host or from the host itself, which has been previously isolated and contacted a nucleic acid of the invention. Alternatively, the isolated cell is a nonpathogenic bacterium or yeast. Preferably, the nonpathogenic bacterium is a *lactobacillus*. The contacting of a nucleic acid of the invention ex vivo with cells previously removed from a given animal, such as a mammal, in particular a human, in such a manner that the nucleic acid will become inserted into the cell, is within the ordinary skill in the art. Such cells express the polypeptide in vivo after reintroduction into the host. The feasibility of such a therapeutic strategy to deliver a therapeutic amount of the polypeptide in close proximity to the desired target cells and pathogens, i.e., virus, more particularly retrovirus, specifically HIV and its envelope glycoprotein gp120, has been demonstrated in studies with cells engineered ex vivo to express sCD4 (Morgan et al. (1994), supra). It is also possible that, as an alternative to ex vivo insertion of a nucleic acid of the invention, such a nucleic acid can be inserted into cells directly in vivo, such as by use of an appropriate viral vector.

Such cells transfected in vivo are expected to produce antiviral amounts of a polypeptide of the invention directly in vivo.

Alternatively, a nucleic acid of the invention can be inserted into suitable nonmammalian cells, and such cells, when administered to a host, will express therapeutic or prophylactic amounts of a polypeptide, fusion protein, or conjugate of the invention directly in vivo within or onto a desired body compartment of the host, in particular an animal such as a human. In a preferred embodiment of the present invention, a method of female-controllable prophylaxis against viral infection, such as HIV infection, comprises the intravaginal administration and/or establishment of, in a female human, a persistent intravaginal population of lactobacilli that have been transformed with a coding sequence of the present invention to produce, over a prolonged time, effective virucidal levels a polypeptide, a fusion protein, or conjugate of the invention directly on or within or onto the vaginal and/or cervical and/or uterine mucosa. It is noteworthy that both of the World Health Organization (WHO), as well as the U.S. National Institute of Allergy and Infectious Diseases, have pointed to the need for development of female-controlled topical microbicides, suitable for blocking the transmission of HIV, as an urgent global priority (Lange et al., *Lancet,* 341: 1356 (1993); and Fauci, NIAID News, Apr. 27, 1995).

The polypeptide, fusion protein, and conjugate of the invention comprise peptides, and, as such, are particularly susceptible to hydrolysis of amide bonds (e.g., catalyzed by peptidases) and disruption of essential disulfide bonds or formation of inactivating or unwanted disulfide linkages (Carone et al., *J. Lab. Clin. Med.,* 100:1-14 (1982)). There are various ways to alter molecular structure, if necessary, to provide enhanced stability to such compounds (Wunsch, *Biopolymers,* 22: 493-505 (1983); and Samanen, in Polymeric Materials in Medication, Gebelein et al., eds., Plenum Press: New York (1985), pp. 227-242), which can be essential for preparation and use of pharmaceutical compositions containing such compounds for therapeutic or prophylactic applications against viruses, e.g., HIV. Possible options for useful chemical modifications include, but are not limited to, the following (adapted from Samanen (1985), supra): (a) olefin substitution, (b) carbonyl reduction, (c) D-amino acid substitution, (d) N-methyl substitution, (e) C-methyl substitution, (f) C—C'-methylene insertion, (g) dehydro amino acid insertion, (h) retro-inverso modification, (I) N-terminal to C-terminal cyclization, and (j) thiomethylene modification. Polypeptides, fusion proteins, and conjugates also can be modified by covalent attachment of carbohydrate and polyoxyethylene derivatives, which are expected to enhance stability and resistance to proteolysis (Abuchowski et al., in Enzymes as Drugs, Holcenberg et al., eds., John Wiley New York (1981), pp. 367-378).

Other important general considerations for design of delivery strategy systems and compositions, and for routes of administration, for protein and peptide drugs, such as those provided by the invention, also apply (see Eppstein, *CRC Crit. Rev. Therapeutic Drug Carrier Systems,* 5: 99-139 (1988); Siddiqui et al., *CRC Crit. Rev. Therapeutic Drug Carrier Systems,* 3: 195-208 (1987); Banga et al., *Int. J. Pharmaceutics,* 48: 15-50 (1988); Sanders, *Eur. J. Drug Metab. Pharmacokinetics,* 15: 95-102 (1990); and Verhoef, *Eur. J. Drug Metab. Pharmacokinetics,* 15: 83-93 (1990). The appropriate delivery system for a polypeptide, fusion protein, or conjugate will depend upon its particular nature, the particular clinical application, and the site of drug action. Especially in the case of oral delivery, but also possibly in conjunction with other routes of delivery, it can be desirable to use an absorption-enhancing agent in combination with a given polypeptide, fusion protein, or conjugate. A wide variety of absorption-enhancing agents have been investigated and/or applied in combination with protein and peptide drugs for oral delivery and for delivery by other routes (Verhoef, 1990, supra; van Hoogdalem, *Pharmac. Ther.,* 44: 407-443 (1989); Davis, *J. Pharm. Pharmacol.,* 44(Suppl. 1): 186-190 (1992)). Most commonly, typical enhancers fall into the general categories of (a) chelators, such as EDTA, salicylates, and N-acyl derivatives of collagen, (b) surfactants, such as lauryl sulfate and polyoxyethylene-9-lauryl ether, (c) bile salts, such as glycholate and taurocholate, and derivatives, such as tauro-di-hydro-fusidate, (d) fatty acids, such as oleic acid and capric acid, and their derivatives, such as acylcarnitines, monoglycerides and diglycerides, (e) non-surfactants, such as unsaturated cyclic ureas, (f) saponins, (g) cyclodextrins, and (h) phospholipids.

Other approaches to enhancing oral delivery of protein and peptide drugs that can be applied to the invention can include aforementioned chemical modifications to enhance stability to gastrointestinal enzymes and/or increased lipophilicity. Alternatively, or in addition, the protein or peptide drug can be administered in combination with other drugs or substances, which directly inhibit proteases and/or other potential sources of enzymatic degradation of proteins and peptides. Yet another alternative approach to prevent or delay gastrointestinal absorption of protein or peptide drugs is to incorporate them into a delivery system that is designed to protect the protein or peptide from contact with the proteolytic enzymes in the intestinal lumen and to release the intact protein or peptide only upon reaching an area favorable for its absorption. A more specific example of this strategy is the use of biodegradable microcapsules or microspheres, both to protect vulnerable drugs from degradation, as well as to effect a prolonged release of active drug (Deasy, in Microencapsulation and Related Processes, Swarbrick, ed., Marcell Dekker, Inc.: New York (1984), pp. 1-60, 88-89, 208-211). Microcapsules also can provide a useful way to effect a prolonged delivery of a protein and peptide drug after injection (Maulding, *J. Controlled Release,* 6: 167-176 (1987)).

There are numerous other potential routes of delivery of a protein or peptide drug, such as the polypeptide, fusion protein, or conjugate of the invention. These routes include intravenous, intraarterial, intrathecal, intracisternal, buccal, rectal, nasal, pulmonary, transdermal, vaginal, ocular, and the like (Eppstein (1988), supra; Siddiqui et al. (1987), supra; Banga et al. (1988), supra; Sanders (1990), supra; Verhoef (1990), supra; Barry, in Delivery Systems for Peptide Drugs, Davis et al., eds., Plenum Press: New York (1986), pp. 265-275; and Patton et al., *Adv. Drug Delivery Rev.,* 8: 179-196 (1992)). With any of these routes, or, indeed, with any other route of administration or application, a protein or peptide drug. When such a reaction is not desirable, it may be necessary to modify the molecule in order to mask immunogenic groups. It also can be possible to protect against undesired immune responses by judicious choice of method of formulation and/or administration. For example, site-specific delivery can be employed, as well as masking of recognition sites from the immune system by use or attachment of a so-called tolerogen, such as polyethylene glycol, dextran, albumin, and the like (Abuchowski et al. (1981), supra; Abuchowski et al., *J. Biol. Chem.,* 252: 3578-3581 (1977); Lisi et al., *J. Appl. Biochem.,* 4: 19-33 (1982); and Wileman et al., *J. Pharm. Pharmacol.,* 38: 264-271 (1986)). Such modifications also can have advantageous effects on stability and half-life both in vivo and ex vivo. Procedures for covalent attachment of molecules, such as polyethylene glycol, dextran, albumin and the like, to proteins as previously described herein are well-known to those skilled in the art, and are extensively documented in the literature (e.g., see Davis et al., In Peptide and Protein Drug Delivery, Lee, ed., Marcel Dekker: New York (1991), pp. 831-864).

Other strategies to avoid untoward immune reactions can also include the induction of tolerance by administration initially of only low doses. In any event, it will be apparent from the present disclosure to one skilled in the art that the skilled artisan can select an advantageous strategy from any of a wide variety of possible compositions, routes of administration, or sites of application.

The inventive compounds and compositions can be used in the context of the inventive method to inhibit viral infection as a result of sexual transmission. When used for the prevention of sexual transmission of viral infection (e.g., HIV infection), the method of the invention can comprise vaginal, rectal, oral, penile, or other topical, insertional, or instillational treatment with (e.g., administration of) a viral infection-inhibiting amount of a polypeptide, fusion protein, or conjugate of the invention, and/or other compound or composition of the invention including viable host cells transformed to express such a compound, alone or in combination with one or more other antiviral agents. Antiviral agents used or being considered for use against sexual transmission include, for example, nonoxynol-9 (Bird, *AIDS,* 5: 791-796 (1991)), gossypol and derivatives (Polsky et al., *Contraception,* 39: 579-587 (1989); Lin, *Antimicrob. Agents Chemother.,* 33: 2149-2151 (1989); and Royer, *Pharmacol. Res.,* 24: 407-412 (1991)), and gramicidin (Bourinbair, Life *Sci./Pharmacol. Lett.,* 54: PL5-9 (1994); and Bourinbair et al., *Contraception,* 49: 131-137 (1994)).

Nonpathogenic commensal bacteria and yeasts also offer an attractive means of in situ delivery of a polypeptide, fusion protein, or conjugate of the invention to prevent sexual transmission of viral infections. For example, lactobacilli readily populate the vagina, and indeed are a predominant bacterial population in most healthy women (Redondo-Lopez et al., *Rev. Infect. Dis.,* 12: 856-872 (1990); Reid et al., *Clin. Microbiol. Rev.,* 3: 335-344 (1990); Bruce and Reid, *Can. J. Microbiol.,* 34: 339-343 (1988); Reu et al., *J. Infect. Dis.,* 171: 1237-1243 (1995); Hilier et al., *Clin. Infect. Dis.,* 16(Suppl 4): S273-S281; and Agnew et al., *Sex. Transm. Dis.,* 22: 269-273 (1995)). Lactobacilli are also prominent, nonpathogenic inhabitants of other body cavities, such as the mouth, nasopharynx, upper and lower gastrointestinal tracts, and rectum.

It is well-established that lactobacilli can be readily transformed using available genetic engineering techniques to incorporate a desired foreign nucleic acid sequence, and that such lactobacilli can be made to express a corresponding desired foreign protein (see, e.g., Hols et al., *Appl. and Environ. Microbiol.,* 60: 1401-1413 (1994)). Therefore, within the context of the present disclosure, it will be appreciated by one skilled in the art that viable host cells containing a nucleic acid sequence or vector of the invention, and/or expressing a polypeptide, fusion protein, or conjugate of the invention, can be used directly as the delivery vehicle to the desired site(s) in vivo. Preferred host cells for such delivery directly to desired site(s), such as, for example, to a selected body cavity, can comprise bacteria. More specifically, such host cells can comprise suitably engineered strain(s) of lactobacilli, enterococci, or other common bacteria, such as *E. coli,* normal strains of which are known to commonly populate body cavities. More specifically, such host cells can comprise one or more selected nonpathogenic strains of lactobacilli, such as those described by Andreu et al. (1995, supra), especially those having high adherence properties to epithelial cells, such as, for example, adherence to vaginal epithelial cells, and suitably transformed using the nucleic acid sequences of the present invention.

As reviewed by McGroarty (*FEMS Immunol. Med. Microbiol.,* 6: 251-264 (1993)) the probiotic or direct therapeutic application of live bacteria, particularly bacteria that occur normally in nature, more particularly lactobacilli, for treatment or prophylaxis against pathogenic bacterial or yeast infections of the urogenital tract, in particular the female urogenital tract, is a well-established concept. However, inventive use of non-mammalian cells, particularly bacteria, more particularly lactobacilli, specifically engineered with a nucleic acid of the invention is heretofore unprecedented as a method of treatment of an animal, specifically a human, to prevent infection by a virus, specifically a retrovirus, more specifically HIV-1 or HIV-2.

One skilled in the art will appreciate that various routes of administering a drug are available, and, although more than one route can be used to administer a particular drug, a particular route can provide a more immediate and more effective reaction than another route. Furthermore, one skilled in the art will appreciate that the particular pharmaceutical carrier employed will depend, in part, upon the particular active compound employed, and the chosen route of administration. Accordingly, there is a wide variety of suitable formulations of the compounds and compositions of the invention.

Formulations suitable for oral administration can consist of liquid solutions, such as an effective amount of the compound dissolved in diluents, such as water, saline, or fruit juice; capsules, sachets or tablets, each containing a predetermined amount of the active ingredient, as solid, granules or freeze-dried cells; solutions or suspensions in an aqueous liquid; oil-in-water emulsions or water-in-oil emulsions; lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels and the like containing, in addition to the active ingredient, such as, for example, freeze-dried lactobacilli or live *lactobacillus* cultures genetically engineered to directly produce a polypeptide, fusion protein, or conjugate of the invention, such carriers as are known in the art. Tablet forms can include one or more of lactose, mannitol, corn starch, potato starch, microcrystalline cellulose, acacia, gelatin, colloidal silicon dioxide, croscaimellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract (see, for example, Wallace et al., *Science,* 260: 912-915 (1993)).

The compounds and compositions of the invention, alone or in combination with other antiviral agents, can be made into aerosol formulations or microparticulate powder formulations to be administered via inhalation. These aerosol formulations can be placed into pressurized acceptable propellants, such as dichlorodifluoromethane, propane, nitrogen and the like.

The compounds and compositions of the invention, alone or in combination with other antiviral agents or modulators of absorption, can be made into suitable foimulations for transdermal application and absorption (Wallace et al. (1993), supra). Transdermal electroporation or iontophoresis also can be used to promote and/or control the systemic delivery of the compounds and/or compositions of the present invention through the skin (e.g., see Theiss et al., *Meth. Find. Exp. Clin. Pharmacol.*, 13: 353-359 (1991)).

Formulations for rectal administration can be presented as a suppository with a suitable base comprising, for example, cocoa butter or a salicylate. Formulations suitable for vaginal administration can be presented as pessaries, tampons, creams, gels, pastes, foams, or spray formulas containing, in addition to the active ingredient, such as, for example, freeze-dried lactobacilli or live *lactobacillus* cultures genetically engineered to directly produce a polypeptide, fusion protein, or conjugate of the invention, such carriers as are known in the art to be appropriate. Similarly, the active ingredient can be combined with a lubricant as a coating on a condom. Indeed, preferably, the active ingredient is applied to and/or delivered by any contraceptive device, including, but not limited to, a condom, a diaphragm, a cervical cap, a vaginal ring and a sponge.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The invention further provides a method of inhibiting a virus in a biological sample or in/on an inanimate object. The method comprises contacting the biological sample or the inanimate object with a viral-inhibiting amount of a polypeptide, fusion protein, or conjugate of the invention, or compositions comprising the polypeptide, fusion protein, or conjugate.

By viral-inhibiting amount is meant an amount of active agent, such as in the range of 0.1-1,000 nM (e.g., 0.5 nM, 1 nM, 10 nM, 50 nM, 100 nM, 200 nM, 400 nM, 500 nM, 600 nM, 800 nM, or ranges thereof), sufficient to inhibit the virus so as to reduce, and desirably eliminate, its infectivity. The method optionally further comprises the prior, simultaneous or subsequent contacting, in the same manner or a different manner, of the biological sample or inanimate object with a substance other than the polypeptide, fusion protein, or conjugate of the invention that is efficacious in inhibiting the virus. The biological sample can be a cell, a tissue, an organ, a vaccine formulation, a bodily fluid, and the like. Bodily fluids include blood and blood products and components, semen (sperm), mucus membrane secretions, saliva, and the like. Preferably the virus that is inhibited is infectious, such as HIV. The inanimate object can be a liquid or a solid. Solids include, for example, a surface, especially the surface of an article of durable or consumable medical or laboratory equipment or supply. Liquids include solutions, suspensions, emulsions, and the like, especially those used in a medical or laboratory setting. The method also can be used for the ex vivo virucidal sterilization of a biological sample or inanimate object for administration or implantation in a patient.

Formulations comprising a polypeptide, fusion protein, or conjugate of the invention suitable for virucidal (e.g., HIV) sterilization of biological samples or inanimate objects can be selected or adapted as appropriate, by one skilled in the art, from any of the aforementioned compositions or formulations. Similarly, foimulations suitable for ex vivo sterilization, or inhibition of virus in a biological sample or in a solution, suspension, emulsion, vaccine formulation or other material, which can be administered to a patient in a medical procedure, can be selected or adapted as appropriate by one skilled in the art, from any of the aforementioned compositions or formulations. However, suitable formulations for sterilization or inhibition of virus in a biological sample or in/on an inanimate object are by no means limited to any of the aforementioned formulations or compositions. For example, such formulations or compositions can comprise a polypeptide, fusion protein, or conjugate of the invention attached to a solid support matrix, to facilitate contacting, or otherwise inhibiting infectious virus in a biological sample or inanimate object such as described above. The solid support matrix can comprise, for example, magnetic beads to facilitate contacting and inhibition of infectious virus, and enable the subsequent magnet-assisted removal of the beads from the biological sample or inanimate object. Alternatively, the solid support matrix can comprise a contraceptive device, such as a condom, a diaphragm, a cervical cap, a vaginal ring or a sponge.

When a solid support matrix is used, the polypeptide or fusion protein of the invention can be attached to the support matrix by any suitable method. For example, the polypeptide can be attached to the support matrix by use of an antibody to the polypeptide or fusion protein, or by conjugation of the polypeptide or fusion protein to at least one effector component suitable for binding to the support matrix. Effector components are previously discussed herein with respect to the conjugate of the invention. Methods of attaching an antibody to a solid support matrix are well-known in the art (see, for example, Harlow and Lane. Antibodies: A Laboratory Manual, Cold Springs Harbor Laboratory: Cold Spring Harbor, N.Y., 1988). Alternatively, the solid support matrix, such as magnetic beads, can be coated with streptavidin, in which the polypeptide, fusion protein, or conjugate of the invention, is biotinylated. The use of biotinylation as a means to attach a desired biologically active protein to a streptavidin-coated support matrix, such as magnetic beads, is well-known in the art.

Other methods of attaching a polypeptide, fusion protein, or conjugate to a solid support matrix can be used. For example, polyethylene glycol can be used to attach such a compound to the matrix. When a polypeptide, fusion protein, or conjugate is attached to the matrix using polyethylene glycol, it is provided with a longer "tether" than would be feasible or possible for other attachment methods, such as biotinylation/streptavidin coupling. A polypeptide, fusion protein, or conjugate of the invention coupled by a polyethylene glycol tether to a solid support matrix (such as magnetic beads, porous surface or membrane, and the like) can permit optimal exposure of a binding surface, epitope, hydrophobic or hydrophilic focus, and/or the like, of the bound compound in a manner that, in a given situation and/or for a particular virus, better facilitates inhibition of the virus.

Similarly, other types of solid support matrices can be used, such as a matrix comprising a porous surface or membrane, over or through which a sample is flowed or percolated, thereby selectively inhibiting infectious virus in the sample. The choice of solid support matrix, means of attachment to the solid support matrix, and means of separating the sample and the matrix-anchored compound will depend, in part, on the sample (e.g., fluid vs. tissue) and the virus to be inhibited. It is expected that the use of a selected coupling molecule can confer certain desired properties to a matrix that can have particularly advantageous properties in a given situation.

The method of the invention also has utility in real time ex vivo inhibition of virus or virus infected cells in a bodily fluid, such as blood, e.g., in the treatment of viral infection, or in the inhibition of virus in blood or a component of blood; for transfusion, in the inhibition or prevention of viral infection; in dialysis, such as kidney dialysis; and in inhibiting virus in sperm obtained from a donor for in vitro and in vivo fertilization. The methods also have applicability in the context of tissue and organ transplantations.

Matrix-anchored antibodies of the invention can be used in a method to inhibit virus in a sample. The antibody can be coupled to a solid support matrix using similar methods and with similar considerations as described above for attaching polypeptides, fusion proteins, or conjugates to a solid support matrix. Preferably, the matrix is a solid support matrix, such as a magnetic bead or a flow-through matrix.

The following examples further illustrate the invention but, of course, should not be construed as in any way limiting its scope.

EXAMPLE 1

This example illustrates viral envelope molecular target interactions of SD1 (SEQ ID NO: 1).

The affinity of the SD1 polypeptide (SEQ ID NO: 1) and the scytovirin polypeptide (SEQ ID NO: 4) for HIV envelope proteins gp120 and gp41 were determined using an ELISA protocol as described in O'Keefe et al., *Mol. Pharmacol.*, 58: 982-992 (2000). For these demonstrations, ELISA protocols were as follows. Briefly, the 100 ng/well of either gp120 and gp41 proteins was bound to a 96-well plate, which was then rinsed with PBS containing 0.05% Tween 20 (TPBS) and blocked with BSA. Between each subsequent step, the plate was again rinsed with TPBS (x3). The wells were incubated with serial dilutions of scytovirin or SD1, followed by incubation with a 1:1000 dilution of anti-scytovirin rabbit polyclonal antibody preparation (see Boyd et al., *Antimicrob. Agents Chemother.*, 41(7): 1521-1530 (1999)). The amount of bound scytovirin or SD1 was determined by adding donkey-anti-rabbit antibodies conjugated to horseradish peroxidase (1:2000 dilution, Amersham Life Sciences, Piscataway, N.J.). Upon addition of the horseradish peroxidase substrate buffer and color formation, the reaction was stopped by the addition of 2M $H_2SO_4$ (after 5 minutes for the gp120 plate and 15 minutes for the gp41 plate) and absorbance was measured at 450 nm for each well.

Analysis of the data indicates that scytovirin and SD1 both appeared to bind gp120 and gp41 with approximately the same affinity (see FIGS. 1 and 2). In contrast, when the same experiment was performed with SD2 (residues 49-95 of scytovirin with a substitution of serine at position 55), SD2 had significantly reduced binding (e.g., about 50% binding to gp120) in comparison to scytovirin.

EXAMPLE 2

This example illustrates antiviral activity, in particular anti-HIV activity, of a scytovirin as it compares to SD1.

An XTT-tetrazolium based assay was used to determine the anti-HIV activity of scytovirin and SD1 against acute HIV-1 infection in CEM-SS cells. The protocol followed was the same as described in Gulakowski et al., *J. Virol. Methods*, 33: 87-100 (1991).

SD1 and scytovirin showed comparable activity against the T-tropic laboratory strain HIV-1$_{RF}$ in CEM-SS cells with $EC_{50}$ values of 6.6 nM and 7.5 nM, respectively. Toxicity to the CEM-SS cell line was not detected for either scytovirin or SD1 at concentrations up to 10,000 nM. In contrast, when the same experiment was performed with SD2 (residues 49-95 of scytovirin with a substitution of serine at position 55), SD2 displayed significantly lower anti-HIV activity than scytovirin with a 40 fold higher $EC_{50}$ than scytovirin.

EXAMPLE 3

This example illustrates the anti-HIV activity and binding activity of SD1(Cys7Ser) deletion mutants.

To examine whether the N- and C-terminus of SD1 are necessary for antiviral activity, a series of deletion mutants were constructed in which two, five, or ten amino acids were deleted from the N-terminus of SD1, or eight amino acids were deleted from the C-terminus of SD1. The deletion mutants were subjected to the XTT-tetrazolium based assay as described in Example 2.

Deletion of two, five, or ten N-terminal amino acids from SD1 completely eliminated antiviral activity, indicating that N-terminal amino acids of SD1 are necessary for maintaining the antiviral activity of SD1. Deletion of the eight amino C-terminal amino acids resulted in a 3- to 7-fold decrease in anti-HIV potency, indicating that these C-terminal amino acids optimize the activity of SD1, but are not necessary in order to retain some anti-viral activity.

To determine the gp120 and gp41 binding pattern of the SD1 deletion mutants, ELISA was performed as described in Example 1. The N-terminal mutants had almost no detectable binding activity with gp120 and gp41. The C-terminal mutant exhibited decreased binding activity as compared to SD1.

EXAMPLE 4

This example illustrates that SD1 retains scytovirin's specificity to bind HIV-1 envelope glycoproteins through specific interactions with substructures of high mannose oligosachharides.

Scytovirnin specifically binds to a α-1-2, α1-2, α1-6-linked tetramannoside, a substructure of oligomannose-8 and -9 found on HIV envelope glycoproteins gp120 and gp41 (Adams et al., *Chem. Biol.*, 11(6): 875-881 (2004)). To determine whether or not SD1 retained this binding specificity, an ELISA experiment was performed to determine if the sugars could inhibit binding to HIV gp120. Briefly, a 96-well plate was prepared as described in Example 1 with glycosylated gp120 or gp41 and 100 ng/well of scytovirin or a scytovirin-derived peptide. The scytovirin-derived peptides were (a) SD1, (b) SD1 with an 8 amino acid C-terminal truncation (SD1(1-40)), and (c) SD2. Each well also contained (a) various concentrations of oligomannose-8, (b) 100 μM of glucose, mannose, galactose, xylose, or N-acytylglucosamine, or (c) 100 μg/well α-acid glycoprotein (to act as a carrier for sialic acid). The plate was then washed and visualized using anti-scytovirin polyclonal antibodies as described in Example 1.

Glucose, mannose, galactose, xylose, N-acytylglucosamine, α-acid glycoprotein with sialic acid were not able to inhibit binding to gp120 of SD1, SD1(1-40), or SD2, thereby indicating that the individual domains of scytovirin retained some level of carbohydrate specificity.

This result was supported by additional experiments demonstrating that oligomannose-8 was able to inhibit the binding of SD1 to gp41 in a concentration-dependent manner. The hypothesis that scytovirin specificity resided in the individual domains of scytovirin (represented by SD1 and SD2) also was confirmed by NMR analysis of a titration of the scytovirin-binding tetrasachharide (Adams et al., supra) into scytovirin.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Any open-ended term (e.g., comprising) used to describe the foregoing invention can be replaced with a closed-ended term (e.g., consisting essentially of, or consisting of) without departing from the spirit and scope of the invention. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments will be apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of inhibiting infection of a host by a virus having a glycoprotein comprising a high mannose oligosaccharide as a surface protein, which method comprises administering to the host a virus-inhibiting amount of a polypeptide comprising the amino acid sequence of SEQ ID NO:1, wherein the high mannose oligosaccharide is oligomannose-8, oligomannose-9, or a combination thereof.

2. The method of claim 1, further comprising the prior, simultaneous, or subsequent administration, by the same route or a different route, of a substance other than the polypeptide that is efficacious in inhibiting the viral infection.

3. The method of claim 1, wherein the virus is an immunodeficiency virus.

4. The method of claim 3 wherein the host is a human and the immunodeficiency virus is human immunodeficiency virus (HIV).

5. The method of claim 1, wherein the polypeptide further comprises a flexible spacer that links the amino acid sequence of SEQ ID NO: 1 to a second amino acid sequence of SEQ ID NO: 1.

6. The method of claim 1, wherein the polypeptide further comprises albumin.

7. The method of claim 1, wherein the polypeptide is part of a conjugate.

8. The method of claim 7, wherein the conjugate further comprises one or more effector components selected from the group consisting of polyethylene glycol, dextran, an antiviral agent, and a solid support matrix.

9. A method of inhibiting a virus having a glycoprotein comprising a high mannose oligosaccharide as a surface protein in a biological sample or in/or an inanimate object, which method comprises contacting the biological sample or the inanimate object with a virus-inhibiting amount of a polypeptide comprising the amino acid sequence of SEQ ID NO:1, wherein the high mannose oligosaccharide is oligomannose-8, oligomannose-9, or a combination thereof.

10. The method of claim 9, further comprising the prior, simultaneous, or subsequent contacting, in the same manner or in a different manner, of the biological sample or inanimate object with a substance other than the polypeptide that is efficacious in inhibiting the virus.

11. The method of claim 9 wherein the biological sample is a bodily fluid, a cell, a tissue, an organ, or a vaccine formulation.

12. The method of claim 9 wherein the polypeptide further comprises a flexible spacer that links the amino acid sequence of SEQ ID NO: 1 to a second amino acid sequence of SEQ ID NO: 1.

13. The method of claim 9 wherein the polypeptide further comprises albumin.

14. The method of claim 9 wherein the polypeptide is part of a conjugate.

15. The method of claim 14, wherein the conjugate further comprises one or more effector components selected from the group consisting of polyethylene glycol, dextran, an antiviral agent, and a solid support matrix.

* * * * *